United States Patent
Rosengren et al.

(10) Patent No.: US 9,359,422 B2
(45) Date of Patent: Jun. 7, 2016

(54) SINGLE CHAIN RELAXIN POLYPEPTIDES

(75) Inventors: Karl Johan Rosengren, Wilston (AU); Linda Maria Haugaard-Kedstrom, St. Lucia (AU); Ross Alexander David Bathgate, Monee Ponds (AU); Mohammed Akhter Hossain, Brunswick West (AU); John Desmond Wade, Parkville (AU); Andrew Lawrence Gundlach, Hawthorn (AU); Andrew J. Lawrence, Parkville (AU)

(73) Assignees: The University of Queensland, Queensland (AU); Howard Florey Institute of Experimental Physiology and Medicine, Parkville, Victoria (AU)

( * ) Notice: Subject to any disclaimer, the term of this patent is extended or adjusted under 35 U.S.C. 154(b) by 0 days.

(21) Appl. No.: 13/821,726

(22) PCT Filed: Sep. 8, 2011

(86) PCT No.: PCT/AU2011/001158
§ 371 (c)(1),
(2), (4) Date: Oct. 17, 2013

(87) PCT Pub. No.: WO2012/031326
PCT Pub. Date: Mar. 15, 2012

(65) Prior Publication Data
US 2014/0038895 A1    Feb. 6, 2014

(30) Foreign Application Priority Data
Sep. 8, 2010   (AU) ................. 2010904046

(51) Int. Cl.
C07K 14/64    (2006.01)
A61K 38/22    (2006.01)
C07H 21/04    (2006.01)
C07K 14/575   (2006.01)
A61K 38/00    (2006.01)

(52) U.S. Cl.
CPC ............ C07K 14/575 (2013.01); C07K 14/64 (2013.01); A61K 38/00 (2013.01)

(58) Field of Classification Search
None
See application file for complete search history.

(56) References Cited

U.S. PATENT DOCUMENTS

2005/0026822 A1* 2/2005 Tregear et al. ............... 514/12
2007/0004619 A1  1/2007 Del Borgo et al.

FOREIGN PATENT DOCUMENTS

WO   WO 2004/113381     12/2004
WO   WO-2008094437 A2   8/2008
WO   WO 2012/031326 A1  3/2012

OTHER PUBLICATIONS

Büllesbach et al. Total synthesis of human relaxin and human relaxin derivatives by solid-phase peptide synthesis and site-directed chain combination. J Biol Chem. Jun. 15, 1991;266(17):10754-61.*
Hossain et al. The structural and functional role of the B-chain C-terminal arginine in the relaxin-3 peptide antagonist, R3(BDelta23-27)R/I5. Chem Biol Drug Des. Jan. 2009;73(1):46-52.*
Tregear et al. The chemistry and biology of human relaxin-3. Ann N Y Acad Sci. May 2005;1041:40-6.*
Bathgate et al., International Union of Pharmacology LVII: Recommendations for the Nomenclature of Receptors for Relaxin Family Peptides. Pharmacol Reviews 58(1):7-31, 2006.
Haugaard-Kedstrom et al., Design, synthesis and characterization of a single-chain peptide antagonist for the relaxin-3 receptor RXFP3. Journal of the American Chemical Society, 133:4965-4974, 2011.
Johnson et al., Heat shock protein 10 inhibits lipopolysaccharide-induced inflammatory mediator production. *J Biol Chem* 280:4037-4047, 2005.
Kuei et al., R3(BA23-27)R/15 chimeric peptide, a selective antagonist for GPCR135 and GPCR142 over relaxin receptor LGR7 in vitro and in vivo characterization. The Journal of Biological Chemistry, 282(35): 25425-25435, 2007.
Morton et al., Production of a recombinant form of early pregnancy factor that can prolong allogeneic skin graft survival time in rats. *Immunol Cell Biol* 78:603-607, 2000.
PCT/AU2011/001158 Written Opinion dated Nov. 14, 2011.
PCT/AU2011/001158 International Search Report dated Nov. 14, 2011.
PCT/AU2011/001158 IPRP dated Mar. 12, 2013.
Ryan et al., Affinity purification, overexpression, and characterization of Chaperonin 10 homologues synthesized with and without N-terminal Acetylation. *J Biol Chem* 270:22037-22043, 1995.
Shaham et al., The reinstatement model of drug relapse: history, methodology and major findings. *Psychopharmacology* 168: 3-20, 2003.
Wishart et al., 1H, 13C and 15N random coil NMR chemical shifts of the common amino acids. I. Investigations of nearest-neighbor effects. *J Biomol NMR*, 5(1):67-81, 1995.
Australia Patent Application No. 2011301146 Examination Report dated Jun. 25, 2015.
EBI Accession No. GSP:ATD29325 (XP-002717447).
Tan et al., Comparison of relaxin receptors in rat isolated atria and uterus by use of synthetic and native relaxin analogues. British Journal of Pharmacology, 123:762-770 (1998).

* cited by examiner

*Primary Examiner* — David Romeo
(74) *Attorney, Agent, or Firm* — Wilson Sonsini Goodrich & Rosati

(57) ABSTRACT

The present invention relates to biologically active single chain relaxin polypeptides comprising a relaxin B chain derived from relaxin-3, the polypeptides being truncated by one or more amino acids at the C-terminus of the relaxin-3 B chain. Typically the single chain relaxin polypeptides are antagonists of the RXFP3 receptor, and in some embodiments are selective antagonists of the RXFP3 receptor.

15 Claims, 8 Drawing Sheets

A

B

A

B

SINGLE CHAIN RELAXIN POLYPEPTIDES

SEQUENCE LISTING

The instant application contains a Sequence Listing which has been submitted in ASCII format via EFS-Web and is hereby incorporated by reference in its entirety. Said ASCII copy, created on Oct. 10, 2013, is named 24103-707.831-SL.txt and is 8,192 bytes in size.

FIELD OF THE INVENTION

The present invention relates generally to biologically active single chain relaxin polypeptides and to nucleic acids encoding the same. The present invention in particular relates to single chain relaxin-3 polypeptides comprising a relaxin-3 derived B chain and which selectively or specifically bind to the RXFP3 (GPCR135) receptor. The invention also relates to uses of polypeptides of the invention, methods employing the same and to compositions comprising such polypeptides.

BACKGROUND OF THE INVENTION

Relaxins are heterodimeric peptide hormones composed, in their mature form, of an A chain and a B chain linked via disulphide bridges. Human relaxins in their mature form are stabilised by three disulphide bonds, two inter-chain disulphide bonds between the A chain and B chain and one intra-chain disulphide bond between cysteine residues in the A chain.

Relaxins have been conserved through vertebrate evolution and have been characterised in a large and diverse range of vertebrate species. In particular the cysteine residues in the B and A chains responsible for the intra- and inter-chain disulphide bonds are highly conserved. Whilst in most species only two forms of relaxin have been identified (relaxin and relaxin-3), in humans three distinct forms of relaxin have been described and the genes and polypeptides characterised. These have been designated H1, H2 and H3. Homologues of H1 and H2 relaxin have been identified in other higher primates including chimpanzees, gorillas and orangutans. Differing expression patterns for H1, H2 and H3 relaxin suggest some differences in biological roles, however all three forms display similar biological activities, as determined for example by their ability to modulate (stimulate or inhibit) cAMP activity in cells expressing relaxin family receptors, and accordingly share some biological functions in common.

Relaxin-3 is predominantly expressed in the brain where it acts as a neuropeptide acting through its receptor RXFP3 as a regulator of homeostatic physiology and complex behaviours, including feeding and metabolism, and circadian arousal and sleep patterns, with strong interactions with brain stress and mood systems.

Aberrant relaxin activity and/or expression is implicated in a number of disorders and diseases and thus there exist a number of important clinical applications for relaxin and antagonists of relaxin receptors.

With the increasing therapeutic promise shown by relaxin-3 and the continued development of potential clinical applications there is also an interest in developing relaxin polypeptides that are simpler in structure than native relaxin molecules and yet which retain the ability to bind to relaxin receptors and/or retain biological activity. Simplifying the structure of therapeutic polypeptides and minimising the amino acid sequence required to impart biological activity on therapeutic polypeptides can serve to reduce the cost of polypeptide synthesis, reduce the complexity and difficulty of synthesis, and/or improve the efficiency of synthesis. Moreover, simplified, smaller molecules may exhibit improved in vivo activities and/or cellular uptake of such molecules may be improved when compared to native counterparts. In the case of relaxins, attention to date has been focused on heterodimeric polypeptides and to date single chain relaxin analogues that retain sufficient biological activity to be of therapeutic potential have not been identified.

The biological actions of relaxins are mediated through G protein coupled receptors (reviewed in Bathgate et al., 2006). To date, H1, H2 and H3 relaxins have been shown to primarily recognise and bind four receptors, RXFP1 (LGR7), RXFP2 (LGR8), RXFP3 (GPCR135) and RXFP4 (GPCR142). Interestingly, receptors RXFP1 and RXFP2 are structurally distinct from receptors RXFP3 and RXFP4, yet despite the differences there is significant cross-reactivity between different native relaxin molecules and different receptors. The endogenous receptor in the brain for H3 relaxin is RXFP3, however H3 relaxin has also been shown in cell-based systems to bind and activate both RXFP1 and RXFP4. Thus, since both RXFP1 and RXFP3 are expressed in the brain, it has been very difficult to experimentally determine the precise physiological role of relaxin-3 in the brain due to its cross-activation of RXFP1. Accordingly, there is a need for analogues of relaxin-3 that are specific for RXFP3, lacking the ability to bind and activate RXFP1 or RXFP4, or that are at least strongly selective for RXFP3.

SUMMARY OF THE INVENTION

Provided herein are novel modified relaxin polypeptides having binding activity at RXFP3, which polypeptides comprise only a relaxin-derived B chain. In particular, single chain modified relaxin polypeptides provided in embodiments of the present invention are antagonists of the RXFP3 receptor. Polypeptides of the invention are "modified" in that they possess B chain amino acid sequences that differ from those found in corresponding native relaxin molecules at one or more positions. Typically the B chain of a modified polypeptide of the present invention is derived from relaxin-3 and comprises one or more amino acid substitutions with respect the corresponding native relaxin-3 B chain.

According to a first aspect there is provided a biologically active single chain relaxin polypeptide comprising a relaxin B chain derived from relaxin-3, the polypeptide being truncated by one or more amino acids at the C-terminus of the relaxin-3 B chain.

Typically the polypeptide is truncated by up to about 5 amino acids at the C-terminus compared to the native relaxin-3 B chain sequence and a basic amino acid is incorporated at the C-terminus of the relaxin-3 derived B chain. Typically the basic amino acid residue is arginine.

In particular embodiments the relaxin-3 is human relaxin-3 (H3 relaxin). The H3 relaxin may comprise a B chain comprising or consisting of an amino acid sequence as set forth in SEQ ID NO:2, or a variant or derivative thereof.

In a particular embodiment, the C-terminal 5 amino acids from the native sequence of the relaxin-3 B chain are replaced by a terminal arginine residue. Thus, where the B chain sequence is derived from human relaxin-3, the C-terminal sequence GGSRW (corresponding to residues 23-27 of SEQ ID NO:2) may be replaced by R.

Typically the single chain polypeptide is further modified such that one or more cysteine residues in the native relaxin-3 B chain sequence are replaced by neutral amino acids, typically serine or alanine, more typically serine. In a particular embodiment, where the B chain sequence is derived from human relaxin-3 the cysteine residues at positions 10 and 22 of the native human relaxin-3 sequence are replaced by serine residues.

The single chain polypeptide typically comprises a C-terminal amide or acid group, more typically a C-terminal amide group.

The single chain polypeptide may further comprise a truncation of one or more amino acids from the N-terminus of the relaxin-3 B chain when compared to the native relaxin-3 sequence. In particular embodiments, the truncation is of up to about 4 amino acids from the N-terminus.

In embodiments of the first aspect the single chain polypeptide comprises or consists of the amino acid sequence set forth in one of SEQ ID NOs:4 to 13, or a variant or derivative thereof.

In a particular embodiment the single chain polypeptide comprises or consists of the amino acid sequence set forth in SEQ ID NO:4, or a variant or derivative thereof.

In particular embodiments the single chain modified relaxin polypeptide of the first aspect is selective or specific for the RXFP3 receptor. In further particular embodiments the polypeptide is an antagonist of the RXFP3 receptor.

A second aspect provides polynucleotides encoding modified relaxin polypeptides according to the first aspect.

A third aspect provides a pharmaceutical composition comprising a modified relaxin polypeptide of the first aspect or a polynucleotide of the second aspect, optionally together with one or more pharmaceutically acceptable carriers, excipients or diluents.

A fourth aspect provides a method for treating or preventing a disease or condition, the method comprising administering to a subject in need thereof a modified relaxin polypeptide of the first aspect, a polynucleotide of the second aspect or a pharmaceutical composition of the third aspect.

In an embodiment the disease or condition may be associated with aberrant expression and/or activity of relaxin or with aberrant expression and/or activity of the RXFP3 receptor. In an alternative embodiment, a modified polypeptide of the invention (or a polynucleotide encoding the same, or a pharmaceutical composition comprising the same) may be administered for the treatment or prevention of a disease or condition wherein the inhibition of biological activity at, or signalling via, the RXFP3 receptor is desirable.

In exemplary embodiments the disease or condition may be selected from Attention Deficit Hyperactivity Disorder (ADHD), obsessive compulsory disorder, autism and Autism Spectrum Disorders (ASD), neuroendocrine disorders of pregnancy and post-partum period (postnatal depression), and medication-related hyperactivity or hyper-arousal conditions.

A fifth aspect provides a method for the prevention or inhibition of substance use, abuse and/or addiction, addictive behaviour, or a symptom, behaviour or condition associated with substance abuse and/or addiction, the method comprising administering to a subject in need thereof an effective amount of a modified relaxin polypeptide of the first aspect, a polynucleotide of the second aspect or a pharmaceutical composition of the third aspect.

The substance may be any addictive substance. In particular embodiments the substance is selected from alcohol, nicotine, an opiate, a cannabinoid, a psychostimulant or an inhalant. The behaviour associated with substance abuse and/or addiction may be a negative behaviour, such as substance use (self-administration) and/or substance seeking behaviour.

A sixth aspect provides the use of a modified relaxin polypeptide of the first aspect, or a polynucleotide of the second aspect for the manufacture of a medicament for the treatment or prevention of a disease or condition, optionally a condition or disorder associated with aberrant expression and/or activity of relaxin or with aberrant expression and/or activity of the RXFP3 receptor, or wherein the inhibition of biological activity at, or signalling via, the RXFP3 receptor is desirable.

A seventh aspect provides the use of a modified relaxin polypeptide of the first aspect, or a polynucleotide of the second aspect for the manufacture of a medicament for the prevention or inhibition of substance use, abuse and/or addiction, addictive behaviour, or a symptom, behaviour or condition associated with substance abuse and/or addiction.

Also provided is the use of a modified relaxin polypeptide of the first aspect, or a polynucleotide of the second aspect in a method for the treatment or prevention of a disease or condition, optionally a condition or disorder associated with aberrant expression and/or activity of relaxin or with aberrant expression and/or activity of the RXFP3 receptor, or wherein the inhibition of biological activity at, or signalling via, the RXFP3 receptor is desirable.

BRIEF DESCRIPTION OF THE DRAWINGS

The present invention is described, by way of non-limiting example only, with reference to the accompanying drawings.

Figure 1:
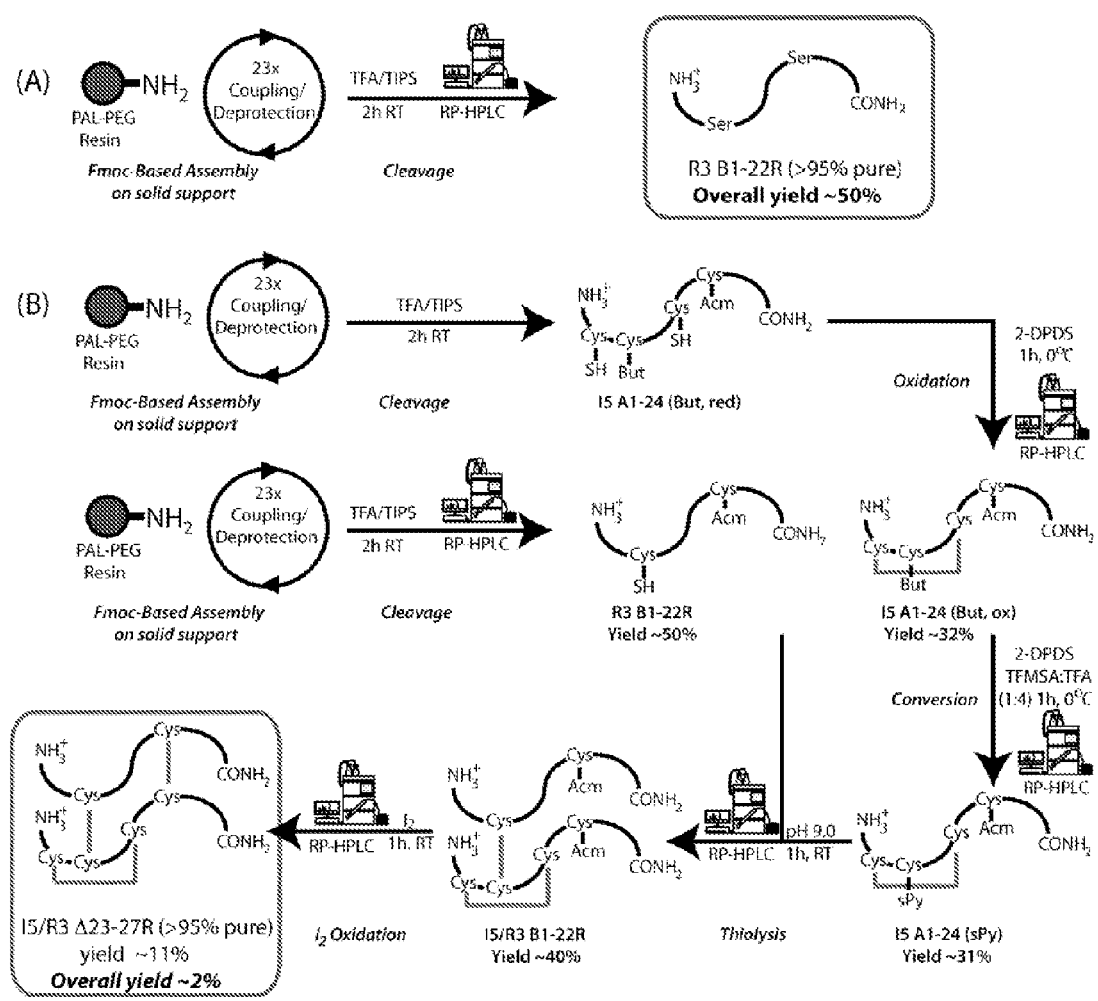
FIG. 1. Comparison of the synthetic routes to the antagonists R3 B1-22R (A) and R3(BΔ23-27)R/I5 (B). R3 1-22R is directly assembled in its final form on resin requiring a single purification step after cleavage. In contrast the generation of the two-chain R3(BΔ23-27)R/I5 antagonist requires assembly of two separate chains, four separate reactions for the regioselective formation of its disulfide bond and typically include five purification steps, resulting in low overall yields.

Amino acid sequences of native human relaxin-3 A and B chains are set forth in SEQ ID NOs: 1 and 2, respectively. SEQ ID NOs: 3 to 13 provide the amino acid sequences of single chain modified relaxin polypeptides as exemplified herein.

DETAILED DESCRIPTION OF THE INVENTION

The articles "a" and "an" are used herein to refer to one or to more than one (i.e., to at least one) of the grammatical object of the article. By way of example, "an element" means one element or more than one element.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

In the context of this specification, the term "about," is understood to refer to a range of numbers that a person of skill in the art would consider equivalent to the recited value in the context of achieving the same function or result.

The term "polypeptide" means a polymer made up of amino acids linked together by peptide bonds. The term "peptide" may also be used to refer to such a polymer although in some instances a peptide may be shorter (i.e. composed of fewer amino acid residues) than a polypeptide. Nevertheless, the terms "polypeptide" and "peptide" are used interchangeably herein.

The term "relaxin polypeptide" as used herein means a polypeptide, whether modified in accordance with the present invention or corresponding to a naturally occurring relaxin molecule which displays biological activity typically associated with relaxin. The level of such relaxin biological activity displayed by a modified polypeptide of the invention may be equivalent to that of a naturally occurring or native relaxin, or may be enhanced or reduced when compared with the activity of a naturally occurring or native relaxin. In the context of the present disclosure, the term "single chain relaxin polypeptide" refers to polypeptides comprising only a relaxin B chain sequence.

The term "modified" as used herein in the context of a relaxin polypeptide means a polypeptide that differs from a naturally occurring or native relaxin polypeptide at one or more amino acid positions of such naturally occurring or native polypeptide.

The term "conservative amino acid substitution" as used herein refers to a substitution or replacement of one amino acid for another amino acid with similar properties within a polypeptide chain (primary sequence of a protein). For example, the substitution of the charged amino acid glutamic acid (Glu) for the similarly charged amino acid aspartic acid (Asp) would be a conservative amino acid substitution. The nature of other conservative amino acid substitutions is well known to those skilled in the art.

As used herein the term "derived" in the context of B chains in modified polypeptides means that the B chain sequence corresponds to, originates from, or otherwise shares significant sequence homology with naturally occurring B chain sequence. In the context of relaxin polypeptides the terms "naturally occurring" and "native" refer to relaxin polypeptides as encoded by and produced from the genome of an organism. For example, in the context of the present disclosure, the term "native H3 relaxin" refers to the native or naturally occurring human relaxin-3 molecule, being a heterodimer comprising an A and a B chain, typically the sequences of which are as shown in SEQ ID Nos:1 and 2, respectively. Those skilled in the art will also understand that by being "derived" from a naturally occurring or native relaxin sequence, the sequence in the modified polypeptide need not be physically constructed or generated from the naturally occurring or native sequence, but may be chemically synthesised such that the sequence is "derived" from the naturally occurring or native sequence in that it shares sequence homology and function with the naturally occurring or native sequence.

As used herein the term "selective" when used in the context of the ability of a modified relaxin polypeptide to bind the RXFP3 receptor, or the ability of a polypeptide to act as an antagonist of RXFP3 receptor function, means that the polypeptide binds the RXFP3 receptor at significantly higher frequency than it binds other receptors, for example the RXFP1 receptor, or the polypeptide antagonises RXFP3 to a significantly greater extent than it antagonises other receptors, for example the RXFP1 receptor. A modified relaxin polypeptide that is "specific" for the RXFP3 receptor is one that possesses no discernable activity at any other receptor. Thus, a modified relaxin polypeptide that is "specific" for RXFP3 is, by definition, selective for RXFP3.

The term "polynucleotide" as used herein refers to a single- or double-stranded polymer of deoxyribonucleotide, ribonucleotide bases or known analogues of natural nucleotides, or mixtures thereof. The term includes reference to the specified sequence as well as to the sequence complimentary thereto, unless otherwise indicated. The terms "polynucleotide" and "nucleic acid" are used interchangeably herein.

As used herein the terms "treating", "treatment", "preventing" and "prevention" refer to any and all uses which remedy a condition or symptoms, prevent the establishment of a condition or disease, or otherwise prevent, hinder, retard, or reverse the progression of a condition or disease or other undesirable symptoms in any way whatsoever. Thus the terms "treating" and "preventing" and the like are to be considered in their broadest context. For example, treatment does not necessarily imply that a patient is treated until total recovery. Similarly, "prevention" dose not necessarily mean that the subject will not eventually contract a particular condition or disease. Rather, "prevention" encompasses reducing the severity of, or delaying the onset of, a particular condition or disease. In the context of some conditions, methods of the present invention involve "treating" the condition in terms of reducing or eliminating the occurrence of a highly undesirable and irreversible outcome of the progression of the condition but may not of itself prevent the initial occurrence of the condition. Accordingly, treatment and prevention include amelioration of the symptoms of a particular condition or preventing or otherwise reducing the risk of developing a particular condition.

As used herein the terms "effective amount" and "effective dose" include within their meaning a non-toxic but sufficient amount or dose of an agent or compound to provide the desired effect. The exact amount or dose required will vary from subject to subject depending on factors such as the species being treated, the age and general condition of the subject, the severity of the condition being treated, the particular agent being administered and the mode of administration and so forth. Thus, it is not possible to specify an exact "effective amount" or "effective dose". However, for any given case, an appropriate "effective amount" or "effective dose" may be determined by one of ordinary skill in the art using only routine experimentation.

The development of potent and selective RXFP3 antagonists, that are synthetically tractable, to facilitate the in vivo characterisation of the neurological role of relaxin-3/RXFP3 and to realise the potential of RXFP3 as a pharmaceutical target, has been an important challenge for relaxin researchers.

Provided herein are modified relaxin polypeptides capable of selectively or specifically binding RXFP3 and inhibiting the function of this receptor (a selective or specific antagonist of RXFP3). As exemplified herein the present inventors have successfully generated a range of biologically active single chain relaxin polypeptides comprising only a modified relaxin-3 derived B chain sequence. In particular it was observed that minimisation of the human relaxin-3 molecule by elimination of the A chain and truncation of the C-terminus of the B chain generates polypeptides that retain high binding affinity for the RXFP3 receptor and which antagonise RXFP3 receptor function. Moreover, such single chain polypeptides are strongly selective for the RXFP3 receptor.

Without wishing to be bound by theory, based on the data in the present study the inventors suggest that addition of the non-native C-terminal arginine residue is a key feature providing the single-chain analogues disclosed herein with high affinity for RXFP3, as a variant lacking this residue displayed no binding to RXFP3 at any of the tested concentrations. Although addition of this arginine residue has been shown previously to be able to increase the affinity of two-chain truncated versions of relaxin-3, it was not anticipated that this modification would be sufficient to provide a single-chain peptide with an affinity similar to native relaxin-3.

An advantage of the modified relaxin-3 polypeptides exemplified herein is that they are considerably simpler in structure than the native human relaxin-3 and previously described relaxin receptor antagonists, being smaller and possessing a single relaxin polypeptide chain.

According to one aspect the present disclosure provides biologically active single chain relaxin polypeptides comprising a relaxin B chain derived from relaxin-3, the polypeptide being truncated by one or more amino acids at the C-terminus of the relaxin-3 B chain. In particular, provided herein are single chain polypeptides truncated by up to about 5 amino acids at the C-terminus of the relaxin-3 B chain compared to the native relaxin-3 B chain sequence and in which an amino acid, typically a basic amino acid, is incorporated at the C-terminus of the relaxin-3 derived B chain in place of the amino acids removed. In accordance with embodiments of the present disclosure 1, 2, 3, 4, 5 or more amino acids present at the C-terminal end of the native relaxin-3 polypeptide sequence from which the single chain modified relaxin polypeptide is derived are omitted. This may be achieved in any one of a number of ways as will be apparent to those skilled in the art, using approaches and methodologies well known to those skilled in the art. While the present disclosure contemplates the C-terminal addition of any amino acid in place of the amino acids deleted, typically the incorporated amino acid is basic, and more typically the basic amino acid is arginine.

In particular embodiments the relaxin-3 is human relaxin-3. In a particular embodiment, the C-terminal 5 amino acids from the native sequence of the relaxin-3 B chain are replaced by a terminal arginine residue. Thus, where the B chain sequence is derived from human relaxin-3, the C-terminal sequence GGSRW (corresponding to residues may be 23-27 of SEQ ID NO:2) may be replaced by a single arginine (R) residue.

The "single chain relaxin polypeptides" of the present disclosure do not include a relaxin- or relaxin superfamily member-derived A chain. However those skilled in the art will appreciate that the term "single chain relaxin polypeptide" simply refers to the absence of an A chain. Polypeptides of the present disclosure may be combined with or linked to (by covalent or other means) one or more additional proteinaceous or non-proteinaceous moieties.

The A chain of native H3 relaxin comprises the amino acid sequence depicted in SEQ ID NO.1 and the B chain of native H3 relaxin comprises the amino acid sequence depicted in SEQ ID NO.2. Accordingly, the B chain amino acid sequences of single chain relaxin polypeptides the subject of the present disclosure may be based on or derived from the amino acid sequence of the B chain of H3 relaxin, for example the sequence depicted in SEQ ID NO:2. However those skilled in the art will also appreciate that the amino acid sequences of B chains from which the modified polypeptides of the invention may be based, or from which the modified polypeptides may be derived, may include variants of this H3 relaxin B chain sequence.

The term "variant" as used herein refers to substantially similar sequences. Generally, polypeptide sequence variants also possess qualitative biological activity in common, such as receptor binding activity. Further, these polypeptide sequence variants may share at least 50%, 55%, 60%, 65%, 70%, 75%, 80%, 85%, 90%, 91%, 92%, 93%, 94%, 95%, 96%, 97%, 98% or 99% sequence identity. Also included within the meaning of the term "variant" are homologues of polypeptides of the disclosure. A homologue is typically a polypeptide from a different species but sharing substantially the same biological function or activity as the corresponding polypeptide disclosed herein. Further, the term "variant" also includes analogues of the polypeptides of the present disclosure, wherein the term "analogue" means a polypeptide which is a derivative of a polypeptide of the disclosure, which derivative comprises addition, deletion, substitution of one or more amino acids, such that the polypeptide typically retains substantially the same function, for example in terms of receptor binding activity. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in a polypeptide although random insertion is also possible with suitable screening of the resulting product. Deletional variants are characterised by the removal of one or more amino acids from the sequence. Substitutional amino acid variants are those in which at least one residue in a sequence has been removed and a different residue inserted in its place. Additions to amino acid sequences may include fusions with other peptides, polypeptides or proteins. Modifications may be made to relaxin polynucleotide sequences, for example via the insertion or deletion of one or more codons, such that modified derivatives of the relaxin polypeptide are generated. Such modifications are also included within the scope of the term "variant". For example, modifications may be made so as to enhance the biological activity or expression level of the relaxin or to otherwise increase the effectiveness of the polypeptide to achieve a desired outcome.

Typically a single chain polypeptide of the invention is modified such that one or more cysteine residues in the native relaxin-3 sequence are replaced by neutral amino acids, typically serine or alanine, more typically serine. In a particular embodiment, where the B chain sequence is derived from human relaxin-3 the cysteine residues at positions 10 and 22 (or corresponding positions) of the native human relaxin-3 sequence are replaced by serine residues. The single chain polypeptide may further comprise a truncation of one or more amino acids from the N-terminus of the relaxin-3 B chain when compared to the native relaxin-3 sequence. In particular embodiments, the truncation is of, for example, 1, 2, 3, 4 or 5 amino acids from the N-terminus. In embodiments where the N-terminus of the B chain sequence of the single chain polypeptide is truncated, typically the truncation is of up to about 4 amino acids. As discussed above in relation the truncation of amino acid residues at the C-terminus, the omission of amino acids normally present at the N-terminus of the relaxin-3 B chain sequence from which the modified polypeptide is derived may be achieved in any one of a number of ways as will be apparent to those skilled in the art, using approaches and methodologies well known to those skilled in the art.

The single chain polypeptide typically comprises an amide (for example —$NH_2$) or acid (for example —OH) group on the exposed end of the C-terminal amino acid residue. In particular embodiments this C-terminal group is an amide group, typically $NH_2$.

As described and exemplified herein a single chain relaxin polypeptide in accordance with embodiments of the present disclosure may comprise or consist of an amino acid sequence as set forth in any one of SEQ ID NOs:4 to 13, or a variant or derivative thereof. In a particular embodiment the single chain polypeptide comprises or consists of the amino acid sequence set forth in SEQ ID NO:4. Those skilled in the art will however appreciate and recognise that the scope of the present disclosure is not limited to the specific single chain relaxin polypeptide sequences exemplified herein, but rather other sequences having the general sequence characteristics set our herein are also contemplated and encompassed.

In the modified polypeptides of the present disclosure the relaxin B chain may be modified from those found in naturally occurring or native relaxin molecules by any number of means well known to those skilled in the art. For example the amino acid sequences may be modified by one or more amino acid insertions, deletions and/or substitutions using recombinant DNA and molecular biology techniques known to those skilled in the art.

The present disclosure contemplates modified relaxin polypeptides in which the A and/or B chains possess one or more amino acid deletions, additions or substitutions in comparison with a corresponding native relaxin polypeptide. Amino acid changes in relaxin polypeptides may be effected by techniques well known to those persons skilled in the relevant art. For example, amino acid changes may be effected by nucleotide replacement techniques which include the addition, deletion or substitution of nucleotides (conservative and/or non-conservative), under the proviso that the proper reading frame is maintained. A conservative substitution denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids which can be substituted for one another include asparagine, glutamine, serine and threonine. The term "conservative substitution" also includes the use of a substituted amino acid in place of an unsubstituted parent amino acid. Exemplary techniques for generating such amino acid insertion, deletion or substitution modifications include random mutagenesis, site-directed mutagenesis, oligonucleotide-mediated or polynucleotide-mediated mutagenesis, deletion of selected region(s) through the use of existing or engineered restriction enzyme sites, and the polymerase chain reaction. Such techniques will be well known to those skilled in the art.

Polypeptides of the disclosure can also be further modified, for instance, by glycosylation, amidation, carboxylation, or phosphorylation, or by the creation of acid addition salts, amides, esters, in particular C-terminal esters, and N-acyl derivatives of the polypeptides. The polypeptides can also be further modified to create polypeptide derivatives by forming covalent or non-covalent complexes with other moieties. Covalently-bound complexes can be prepared by cross-linking the chemical moieties to functional groups on the side chains of amino acids comprising the peptides, or at the N- or C terminus. For example, as polypeptide sequence minimisation is often accompanied by increased susceptibility to enzymatic attack and degradation with a corresponding decrease in plasma half life and in vivo activity, a modified polypeptide of the present disclosure may be generated with a polyethylene moiety conjugated at one or more locations (PEGylation) to increase in vivo half life of the polypeptide. Those skilled in the art will appreciate that a number of other well known approaches exist to extend the in vivo half life of polypeptides, such as for example the addition of albumin affinity tags, and the present disclosure is not limited by reference to the exemplary means specifically discussed herein.

Further, the polypeptides of the present disclosure can be conjugated to a reporter group, including, but not limited to a radiolabel, a fluorescent label, an enzyme (e.g., that catalyzes a colorimetric or fluorometric reaction), a substrate, a solid matrix, or a carrier (e.g., biotin or avidin). These are merely exemplary additional modifications that may be made to the modified polypeptides of the invention. Those skilled in the art will appreciate that further modifications may also be made so as to generate analogues of the polypeptides of the present disclosure. By way of example only, illustrative analogues and processes for preparing the same are described in International patent application published as WO 2004/113381, the disclosure of which is incorporated herein by reference in its entirety.

Amino acid additions may also result from the fusion of a relaxin polypeptide or fragment thereof with a second polypeptide or peptide, such as a polyhistidine tag, maltose binding protein fusion, glutathione S transferase fusion, green fluorescent protein fusion, or the addition of an epitope tag such as FLAG or c-myc.

The present disclosure also contemplates fragments and variants of the polypeptides disclosed herein.

The term "fragment" refers to a polypeptide molecule that encodes a constituent or is a constituent of a polypeptide of the disclosure or variant thereof. Typically the fragment possesses qualitative biological activity in common with the polypeptide of which it is a constituent. The peptide fragment may be between about 5 to about 150 amino acids in length, between about 5 to about 100 amino acids in length, between about 5 to about 50 amino acids in length, or between about 5 to about 25 amino acids in length. Alternatively, the peptide fragment may be between about 5 to about 15 amino acids in length.

Relaxin polypeptides modified at the N- and/or C-terminus by the addition, deletion or substitution of one or more amino acid residues as described above also fall within the scope of the present invention.

In accordance with the present disclosure modified relaxin polypeptides may be produced using standard techniques of recombinant DNA and molecular biology that are well known to those skilled in the art. Guidance may be obtained, for example, from standard texts such as Sambrook et al., *Molecular Cloning: A Laboratory Manual*, Cold Spring Harbor, N.Y., 1989 and Ausubel et al., *Current Protocols in Molecular Biology*, Greene Publ. Assoc. and Wiley-Intersciences, 1992. Methods described in Morton et al., 2000 (*Immunol Cell Biol* 78:603-607), Ryan et al., 1995 (*J Biol Chem* 270:22037-22043) and Johnson et al., 2005 (*J Biol Chem* 280:4037-4047) are examples of suitable purification methods for relaxin polypeptides, although the skilled addressee will appreciate that the present invention is not limited by the method of purification or production used and any other method may be used to produce relaxin for use in accordance with the methods and compositions of the present disclosure. Relaxin peptide fragments may be produced by digestion of a polypeptide with one or more proteinases such as endoLys-C, endoArg-C, endoGlu-C and staphylococcus V8-protease. The digested peptide fragments can be purified by, for example, high performance liquid chromatographic (HPLC) techniques.

The purification of modified relaxin polypeptides of the present disclosure may be scaled-up for large-scale production purposes. For this purpose a range of techniques well known to those skilled in the art are available.

Modified relaxin polypeptides of the present disclosure, as well as fragments and variants thereof, may also be synthesised by standard methods of liquid or solid phase chemistry well known to those of ordinary skill in the art. For example such molecules may be synthesised following the solid phase chemistry procedures of Steward and Young (Steward, J. M. & Young, J. D., Solid Phase Peptide Synthesis. (2nd Edn.) Pierce Chemical Co., Illinois, USA (1984).

In general, such a synthesis method comprises the sequential addition of one or more amino acids or suitably protected amino acids to a growing peptide chain. Typically, either the amino or carboxyl group of the first amino acid is protected by a suitable protecting group. The protected amino acid is then either attached to an inert solid support or utilised in solution by adding the next amino acid in the sequence having the complimentary (amino or carboxyl) group suitably protected and under conditions suitable for forming the amide linkage. The protecting group is then removed from this newly added amino acid residue and the next (protected) amino acid is added, and so forth. After all the desired amino acids have been linked, any remaining protecting groups, and if necessary any solid support, is removed sequentially or concurrently to produce the final polypeptide.

Embodiments of the present disclosure also provide isolated polynucleotides encoding relaxin polypeptides as described above, and variants and fragments of such polynucleotides.

Those skilled in the art will appreciate that heterologous expression of polypeptides may be improved by optimising the codons for the particular species in which the relaxin polypeptide is to be expressed. Accordingly, polynucleotides encoding relaxin polypeptides of the present disclosure may be codon-optimised for expression in a particular species.

Fragments of polynucleotides of the invention are also contemplated. The term "fragment" refers to a nucleic acid molecule that encodes a constituent or is a constituent of a polynucleotide of the invention. Fragments of a polynucleotide do not necessarily need to encode polypeptides which retain biological activity. Rather the fragment may, for example, be useful as a hybridization probe or PCR primer. The fragment may be derived from a polynucleotide of the invention or alternatively may be synthesized by some other means, for example chemical synthesis. Polynucleotides of the invention and fragments thereof may also be used in the production of antisense molecules using techniques known to those skilled in the art.

In particular embodiments, polynucleotides of the present disclosure may be cloned into a vector. The vector may be a plasmid vector, a viral vector, or any other suitable vehicle adapted for the insertion of foreign sequences, their introduction into eukaryotic cells and the expression of the introduced sequences. Typically the vector is a eukaryotic expression vector and may include expression control and processing sequences such as a promoter, an enhancer, ribosome binding sites, polyadenylation signals and transcription termination sequences.

The present disclosure also provides antibodies that selectively bind to the modified relaxin polypeptides of the disclosure, as well as fragments and analogues thereof. Suitable antibodies include, but are not limited to polyclonal, monoclonal, chimeric, humanised, single chain, Fab fragments, and an Fab expression library. Antibodies of the present invention may act as agonists or antagonists of relaxin polypeptides, or fragments or analogues thereof.

Methods for the generation of suitable antibodies will be readily appreciated by those skilled in the art. For example, an anti-relaxin monoclonal antibody, typically containing Fab portions, may be prepared using the hybridoma technology described in Antibodies—A Laboratory Manual, Harlow and Lane, eds., Cold Spring Harbor Laboratory, N.Y. (1988).

Screening for the desired antibody can also be accomplished by a variety of techniques known in the art. Assays for immunospecific binding of antibodies may include, but are not limited to, radioimmunoassays, ELISAs (enzyme-linked immunosorbent assay), sandwich immunoassays, immunoradiometric assays, gel diffusion precipitation reactions, immunodiffusion assays, in situ immunoassays, Western blots, precipitation reactions, agglutination assays, complement fixation assays, immunofluorescence assays, protein A assays, and immunoelectrophoresis assays, and the like (see, for example, Ausubel et al., eds, 1994, Current Protocols in Molecular Biology, Vol. 1, John Wiley & Sons, Inc., New York). Antibody binding may be detected by virtue of a detectable label on the primary anti-relaxin antibody. Alternatively, the anti-relaxin antibody may be detected by virtue of its binding with a secondary antibody or reagent which is appropriately labelled. A variety of methods are known in the art for detecting binding in an immunoassay and are within the scope of the present invention.

Single chain relaxin polypeptides and polynucleotides of the present disclosure may be useful as therapeutic agents. Antibodies to the modified relaxin polypeptides of the present disclosure may also be useful as therapeutic agents.

It is known that G-protein coupled receptors such as RXFP3 may be altered, in expression and or activation, in a variety of disease states and hence represent potential targets for the development of novel therapeutics. The ability of the single chain relaxin polypeptides of the present disclosure to bind to the RXFP3 receptor with high affinity and to selectively antagonise this receptor indicate that these polypeptides may be developed as therapeutics for the treatment of conditions and disorders associated with aberrant, typically upregulated, expression and/or activity of the RXFP3 receptor. Single chain relaxin polypeptides as disclosed herein, and polynucleotides encoding the same, may also be useful as therapeutic agents in any circumstance where the inhibition of the activity or signalling from the RXFP3 receptor is desirable.

By way of example, selective RXFP3 antagonists such as the single chain polypeptides of the present disclosure find application in the treatment of substance use, abuse and/or addiction (including drug, alcohol and nicotine addiction), addictive behaviour and symptoms and conditions associated with substance abuse and addiction, as exemplified herein. A key problem with alcoholism, as with substance addiction in general, is the chronically relapsing nature of the disorder. This behaviour pattern can be effectively modelled in rodents, where numerous studies have demonstrated the ability of drug priming, psychological stress or the re-presentation of cues previously associated with drug availability to reinstate drug-seeking behaviour following extinction, even in the absence of subsequent drug rewards. Moreover, despite differences between these means of reinstating previously extinguished behaviour, there is thought to be good general correspondence between animal studies of reinstatement and human experience of relapse (Shaham et al., 2003). The present inventors have developed models of cue-driven relapse to drug-seeking that collectively incorporate the varying human experience. As exemplified herein the single chain modified relaxin polypeptide antagonist B1-22R is able to regulate self-administration of alcohol in alcohol-preferring rats.

Exemplary addictive substances to which embodiments of the disclosure relate include, but are not limited to alcohol, opiates, cannabinoids, nicotine, inhalants and psychostimulants such as cocaine, amphetamine and methamphetamine. In particular embodiments the substance is selected from alcohol and opiates. Addiction to substances such as alcohol, opiates, cannabinoids, nicotine and psychostimulants is typically associated with a number of adverse or negative behaviours exhibited by addicts, which behaviours may serve to exacerbate, prolong or induce relapse into use or abuse of the substance, reinforce or exacerbate the addiction, or induce relapse into addiction and addictive behaviour patterns. Embodiments of the present disclosure provide methods and compositions for the prevention and inhibition of such negative behaviours including, but not limited to the desire to consume the substance and substance-seeking behaviour. Other examples of negative behaviours associated with substance use or addiction include anxiety, dysphoria, stress reactivity and cue reactivity. Embodiments disclosed herein also provide for the treatment of the substance abuse or addiction.

As selective RXFP3 antagonists, the single chain polypeptides disclosed herein also find application in the treatment of Attention Deficit Hyperactivity Disorder (ADHD), obsessive compulsory disorder, autism and Autism Spectrum Disorders (ASD), neuroendocrine disorders of pregnancy and post-partum period (postnatal depression), and medication-related hyperactivity or hyper-arousal conditions.

Without wishing to be bound by theory, the inventors suggest that 'normal' relaxin-3 signaling in the brain is advantageous in survival and is thought to broadly increase arousal, attention, motivation and promote learning and memory, for example. However in pathological situations, when the stress system is hyperactive and dysfunctional, relaxin-3 signaling might be overstimulated. If this is chronic, ongoing hyperactive relaxin-3 signalling (i.e. ongoing elevated levels of relaxin-3 in the brain) becomes detrimental to health, and an antagonist thus becomes therapeutically useful.

Single chain relaxin polypeptides of the present disclosure may also be employed as tools for the study of relaxin-3 biological activities.

In general, suitable compositions for use in accordance with the methods of the single chain polypeptides of the present disclosure may be prepared according to methods and procedures that are known to those of ordinary skill in the art and accordingly may include a pharmaceutically acceptable carrier, diluent and/or adjuvant.

Compositions may be administered by standard routes. In general, the compositions may be administered by the parenteral (e.g., intravenous, intraspinal, subcutaneous or intramuscular), oral or topical route. Administration may be systemic, regional or local. The particular route of administration to be used in any given circumstance will depend on a number of factors, including the nature of the condition to be treated, the severity and extent of the condition, the required dosage of the particular compound to be delivered and the potential side-effects of the compound.

In general, suitable compositions may be prepared according to methods which are known to those of ordinary skill in the art and may include a pharmaceutically acceptable diluent, adjuvant and/or excipient. The diluents, adjuvants and excipients must be "acceptable" in terms of being compatible with the other ingredients of the composition, and not deleterious to the recipient thereof.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

Compositions may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, in a form suitable for parenteral administration, that is, subcutaneous, intramuscular or intravenous injection.

For administration as an injectable solution or suspension, non-toxic parenterally acceptable diluents or carriers can include, Ringer's solution, isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

For the purposes of the present disclosure molecules and agents may be administered to subjects as compositions either therapeutically or preventively. In a therapeutic application, compositions are administered to a patient already suffering from a disease, in an amount sufficient to cure or at least partially arrest the disease and its complications. The composition should provide a quantity of the molecule or agent sufficient to effectively treat the patient.

The therapeutically effective dose level for any particular patient will depend upon a variety of factors including: the disorder being treated and the severity of the disorder; activity of the molecule or agent employed; the composition employed; the age, body weight, general health, sex and diet of the patient; the time of administration; the route of administration; the rate of sequestration of the molecule or agent; the duration of the treatment; drugs used in combination or coincidental with the treatment, together with other related factors well known in medicine.

One skilled in the art would be able, by routine experimentation, to determine an effective, non-toxic amount of agent or compound which would be required to treat applicable diseases and conditions.

Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 mg/m$^2$. Generally, an effective dosage is expected to be in the range of about 25 to about 500 mg/m$^2$, preferably about 25 to about 350 mg/m$^2$, more preferably about 25 to about 300 mg/m$^2$, still more preferably about 25 to about 250 mg/m$^2$, even more preferably about 50 to about 250 mg/m$^2$, and still even more preferably about 75 to about 150 mg/m$^2$.

Typically, in therapeutic applications, the treatment would be for the duration of the disease state.

Further, it will be apparent to one of ordinary skill in the art that the optimal quantity and spacing of individual dosages will be determined by the nature and extent of the disease state being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests.

Embodiments of the present disclosure also contemplate the administration of a polynucleotide encoding a single chain relaxin polypeptide of the disclosure. In such situations the polynucleotide is typically operably-linked to a promoter such that the appropriate polypeptide sequence is produced following administration of the polynucleotide to the subject. The polynucleotide may be administered to subjects in a vector. The vector may be a plasmid vector, a viral vector, or any other suitable vehicle adapted for the insertion of foreign sequences, their introduction into eukaryotic cells and the expression of the introduced sequences. Typically the vector is a eukaryotic expression vector and may include expression control and processing sequences such as a promoter, an enhancer, ribosome binding sites, polyadenylation signals and transcription termination sequences. The nucleic acid construct to be administered may comprise naked DNA or may be in the form of a composition, together with one or more pharmaceutically acceptable carriers.

Those skilled in the art will appreciate that in accordance with the methods of the present disclosure relaxin polypeptides may be administered alone or in conjunction with one or more additional agents. Additionally, the present disclosure contemplates combination therapy using relaxin polypeptides disclosed herein in conjunction with other therapeutic approaches to the treatment of diseases and disorders. For such combination therapies, each component of the combination therapy may be administered at the same time, or sequentially in any order, or at different times, so as to provide the desired effect. Alternatively, the components may be formulated together in a single dosage unit as a combination product. When administered separately, it may be preferred for the components to be administered by the same route of administration, although it is not necessary for this to be so.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present invention will now be described with reference to the following specific examples, which should not be construed as in any way limiting the scope of the invention.

EXAMPLES

Example 1

Single Chain Relaxin-3 Polypeptide Construction

Synthetic single chain relaxin-3 polypeptides were generated by solid phase peptide synthesis. The amino acid sequences of the molecules constructed are shown below in Table 1. The sequences are also provided in the formal Sequence Listing appearing at the end of this specification under the SEQ ID Nos as indicated in the table.

TABLE 1

Single chain relaxin polypeptide sequences

| NAME | SEQUENCE[1] | SEQ ID NO. |
|---|---|---|
| H3 relaxin A chain | DVLAGLSSSCCKWGCSKSEISSLC-NH$_2$ | 1 |
| H3 relaxin B chain | RAAPYGVRLCGREFIRAVIFTCGGSRW-NH$_2$ | 2 |
| H3 B-chain C10/22S | RAAPYGVRLSGREFIRAVIFTSGGSRW-OH | 3 |
| H3 B1-22R | RAAPYGVRLSGREFIRAVIFTSR-NH$_2$ | 4 |
| H3 B1-22R C10/22A | RAAPYGVRLAGREFIRAVIFTAR-NH$_2$ | 5 |
| H3 B1-22R Acid | RAAPYGVRLSGREFIRAVIFTSR-OH | 6 |
| H3 B1-22 | RAAPYGVRLSGREFIRAVIFTS-NH$_2$ | 7 |
| H3 B2-22R | AAPYGVRLSGREFIRAVIFTSR-NH$_2$ | 8 |
| H3 B3-22R | APYGVRLSGREFIRAVIFTSR-NH$_2$ | 9 |
| H3 B4-22R | PYGVRLSGREFIRAVIFTSR-NH$_2$ | 10 |
| H3 B5-22R | YGVRLSGREFIRAVIFTSR-NH$_2$ | 11 |
| H3 B6-22R | GVRLSGREFIRAVIFTSR-NH$_2$ | 12 |
| H3 B7-22R | VRLSGREFIRAVIFTSR-NH$_2$ | 13 |

[1]Residues shown in bold indicate replacements of the cysteine (C) residues found at positions 10 and 22 of the native H3 relaxin B chain. The C-terminal 5 amino acids (GGSRW, corresponding to residues 23-27 of SEQ ID NO: 2) deleted from the H3 B chain to generate B1-22R and subsequent single chain polypeptides is shown highlighted in grey. Underlined residues show the arginine (R) residue incorporated at the C-terminal end of single chain polypeptides Polypeptides were synthesised as follows:

All amino acids were purchased from either Auspep Pty. Ltd (Melbourne, Australia) or GL Biochem (Shanghai, China). Solvents and chemicals were of analytical or peptide synthesis grade.

Peptides were synthesised on either an automatic PerSeptive Biosystems Pioneer continuous flow peptide synthesiser or on an automated microwave assisted peptide synthesiser using standard 9-fluorenylmethoxycarbonyl (Fmoc) peptide chemistry and protocols. All amino acids were of L-Fmoc acid labile type. Fmoc-PAL-PEG-PS or Fmoc-L-Arg(Pbf)-PEG-PS were used as solid support. In brief, the resin was swelled in dimethylformamide (DMF) for 1 h. For the continuous flow peptide synthesiser 4 eq amino acids were dissolved in four fold access of 0.5 M 2-(6-Chloro-1H-benzotriazole-1-yl)-1,1,3,3-tetramethylaminium hexafluorophosphate (HCTU) and 1 M diisopropylethylamine (DIPEA) before addition to the resin. For synthesis using the microwave assisted peptide synthesiser 4 eq of amino acids were dissolved in DMF and added to the resin, followed by addition of four fold access of 0.5 M O-(benzotriazol-1-yl)-N,N,N',N'-tetramethyluronium hexafluorophosphate (HBTU) and 1 M DIPEA. The coupling time was varied between 30-60 min depending on residue. Fmoc deprotection was achieved by treatment with 20% piperidine in DMF for 5 min. Cleavage from the solid support was performed using 94% trifluoro acetic acid (TFA), 2.5% 3,6-dioxa-1,8-octanedithiol (DODT), 2.5% H$_2$O and 1% triisopropylsilane (TIPS) for 2 h. After the cleavage, the resin was filtered off and TFA was evaporated off using N2 (g). The crude peptide was precipitated in diethylether and centrifuged down. This procedure was repeated three times. The peptides were purified by RP-HPLC using a C18 column with a gradient of A (99.9% water and 0.1% TFA) and B (99.9% ACN and 0.1% TFA). The purified peptides were freeze-dried and stored at –20° C. The purity of the peptides were analysed using MALDI-TOF and RP-HPLC.

To determine the peptide content for each synthesised peptide, the peptides were subjected to vapour phase hydrolysis using 6 M HCl containing 2% phenol for 24 h at 110° C. Derivatisation was performed using Water AccQ-Tag kit. Derivatised amino acids were separated using a Shim-Pak XR-ODS column on a RP-HPLC system. Norvaline was used as an internal standard.

From a synthetic point of view the development of the R3 B1-22R peptide represents a dramatic improvement over the currently used R3(BΔ23-27)R/I5 chimeric peptide. FIG. 1 provides a comparison of the synthetic routes towards the final peptides and highlights typical yields relative to the crude material obtained after resin cleavage. The R3 B1-22R peptide is assembled in its final form on resin and requires a single purification step after cleavage, giving yields of ~50%. In contrast, although the B-chain with selectively protected Cys side chains can be assembled and purified with similar efficiency in the production of R3(BΔ23-27)R/I5, it has to subsequently be cross-linked to the A-chain through a two step process resulting in an overall yield relative to the crude B-chain of ~2%. Moreover, the process requires separate assembly of the INSL5 A-chain followed by oxidation and conversion prior to the chain combination step, thus relative to the crude A-chain the overall yield is only ~0.5%. In addition to the losses through the multiple steps R3(BΔ23-27)R/I5 comprise nearly twice as many residues as R3 B1-22R, increasing the number of coupling and deprotection reactions, and typically requires five purification steps. Thus, in comparison the cost of production of R3 B1-22R both in terms of time and chemicals is fractional.

Example 2

Biological Activities of Single Chain Relaxin Polypeptides Against RXFP3

The inventors tested the ability of the single chain relaxin-3 B chain derived polypeptides from Example 1 to bind to the relaxin-3 cognate receptor RXFP3 and also the ability of the polypeptides to agonise or antagonise the functioning of this receptor.

Assays

Binding assays were carried out as follows. HEK-293T cells stably transfected with human RXFP3 were plated out onto pre-coated poly-L-lysine 96-well viewplates with a density of 50 000 cells per well. Media was aspirated off and the cells were washed with PBS before different concentrations of peptide diluted in binding buffer (100 mM HEPES, pH 7.6, 5 mM KCl, 1.3 mM $MgSO_4$, 1.5 mM NaOAc, 1 mM EDTA and 10 mM glucose) and 300 µM of Eu-DTPA-R3/15 was added to each well. The cells were incubated at room temperature for 60 min before the peptide solution was aspirated off and the cells washed with PBS. DELFIA enhancement solution was then added and the cells incubated for a further 30-60 min at room temperature, after which the fluorescence was measured using a time resolved fluorometer with excitation at 340 nm an emission at 614 nm.

For activity determination, a cAMP activity assay was used. CHO cells were cultured in a 1:1 mixture of Dulbecco's modified Eagle's medium and HAMNS-F12 medium supplemented with 10% fetal bovine serum, 1% L-glutamine and 1% penicillin/strepicillin and cultivated in a humidified chamber with 5% $CO_2$ at 37.8° C. 20 000 cells per well were seeded into a pre-coated poly-L lysine 96-wells plate. Cells were incubated over night before being transfected with the mammalian expression vector pcDNA3.1(+)zeo (UMR cDAN Resource Center) carrying human RXFP3 together with a pCRE β-galactosidase reporter plasmid using TransIT-CHO, OptiMEM and CHO-MOJO reagents. Cells were then incubated over night in a humidified chamber with 5% $CO_2$ at 37.8° C. before cAMP assays were performed. A cAMP response was induced by addition of 5 µM forskolin and the ability of the peptides to either reduce this response by activating RXFP3 or restore this response by inhibiting the action of simultaneously added native H3 relaxin measured. In brief, the cells were incubated with the peptide for 6 h in a humidified chamber before the media was aspirated off and the cells were frozen at −80° C. To develop the results, the cells were lysed by addition of 25 µl buffer A (5 ml 10 mM sodium phosphate buffer, pH 8.0, 1 ml 0.2 mM $MgSO_4$ and 50 µl 0.01 mM $MnCl_2$ in 44 ml $H_2O$) to each well and incubated on a shaker for 10 min at room temperature before addition of 100 µl Buffer B (5 ml 100 mM sodium phosphate buffer, pH 8.0, 1 ml 2 mM $MgSO_4$, 50 µl 0.1 mM $MnCl_2$, 2.5 ml 0.5% Triton X-100 and 0.16 ml 40 mM β-mercaptoethanol in 41.3 ml $H_2O$) followed by a 10 min incubation. The substrate, chlorophenol red-β-D-galactopyranoside (CPRG), was then added to each well and the reaction was left at room temperature until a absorbance of <1 AU at 570 nm was reached.

Results

Figure 2:
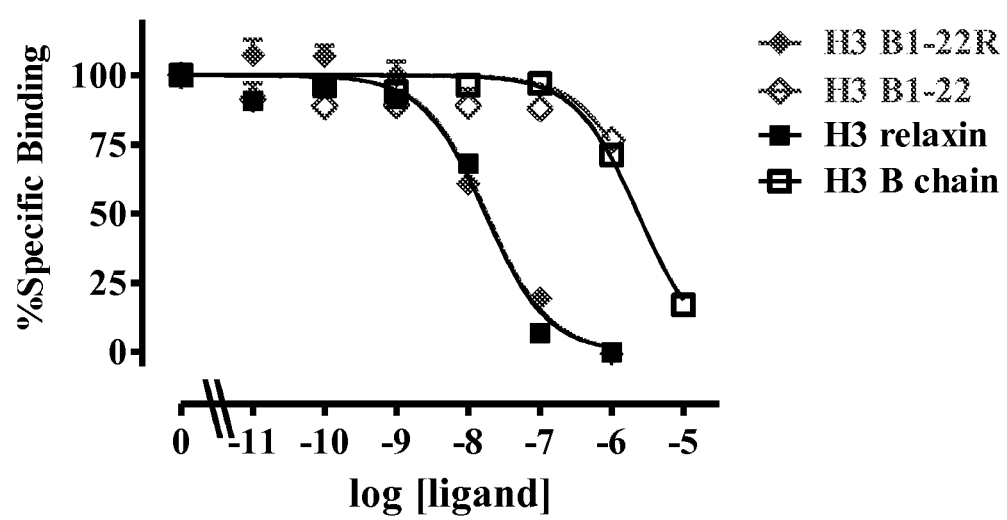
FIG. 2. Binding of native H3 relaxin, H3 relaxin B chain and exemplary single chain relaxin polypeptides H3 B1-22R and H3 B1-22 to human RXFP3 (GPCR135)-expressing cells in the presence of europium (Eu)-labelled H3/INSL5 chimeric polypeptide. Results are the average of three independent experiments.

The ability of the single chain polypeptides B1-22R and B1-22 to bind to the RXFP3 receptor was compared to that of native H3 relaxin (heterodimer) and the native H3 relaxin B chain sequence. As shown in FIG. 2, the single chain polypeptide B1-22R displayed similar binding affinity for RXFP3 as native H3 relaxin, while both B1-22 and the native H3 B chain were significantly less efficient in binding this receptor. These results clearly demonstrate that the addition of the arginine (R) residue to the C-terminal of the truncated B1-22 sequence is required for RXFP3 binding activity.

Similar to the results observed with B1-22R, the single chain polypeptides B1-22R acid, B1-22R (C10/22A), B2-22R, B3-22R, B4-22R, B5-22R and B6-22R and B7-22R also failed to show any agonist activity at the RXFP3 receptor (data not shown). Interestingly, each of these single chain polypeptides with the exception of B7-22R displayed binding affinities for RXFP3 similar to that of B1-22R. B7-22R failed to bind RXFP3 at any detectable level.

A summary of the relative binding affinities (pKi) of the single chain relaxin polypeptides synthesised in the present study (see Example 1, Table 1) for RXFP3 is provided in Table 2 below, in comparison to the binding affinity of native (heterodimeric) human relaxin-3.

TABLE 2

Summary of binding affinities (pKi) of single chain relaxin polypeptides shown in Table 1

| NAME | SEQUENCE | SEQ ID NO. | pIC50 (n = 3) |
|---|---|---|---|
| Native H3 (A + B chain) | DVLAGLSSSCCKWGCSKSEISSLC-$NH_2$<br>RAAPYGVRLCGREFIRAVIFTCGGSRW-$NH_2$ | 1,<br>2 | 6.94 ± 0.07 |
| H3 B-chain C10/22S | RAAPYGVRLSGREFIRAVIFTSGGSRW-OH | 3 | 5.60 ± 0.09 |
| H3 B1-22R | RAAPYGVRLSGREFIRAVIFTSR-$NH_2$ | 4 | 7.75 ± 0.05 |
| H3 B1-22R C10/22A | RAAPYGVRLAGREFIRAVIFTAR-$NH_2$ | 5 | 6.83 ± 0.10 |
| H3 B1-22R Acid | RAAPYGVRLSGREFIRAVIFTSR-OH | 6 | 6.46 ± 0.14 |
| H3 B1-22 | RAAPYGVRLSGREFIRAVIFTS-$NH_2$ | 7 | No activity |
| H3 B2-22R | AAPYGVRLSGREFIRAVIFTSR-$NH_2$ | 8 | 7.06 ± 0.07 |
| H3 B3-22R | APYGVRLSGREFIRAVIFTSR-$NH_2$ | 9 | 6.71 ± 0.17 |
| H3 B4-22R | PYGVRLSGREFIRAVIFTSR-$NH_2$ | 10 | 6.66 ± 0.18 |
| H3 B5-22R | YGVRLSGREFIRAVIFTSR-$NH_2$ | 11 | 6.37 ± 0.19 |
| H3 B6-22R | GVRLSGREFIRAVIFTSR-$NH_2$ | 12 | 6.33 ± 0.17 |
| H3 B7-22R | VRLSGREFIRAVIFTSR-$NH_2$ | 13 | No activity |

Figure 3:
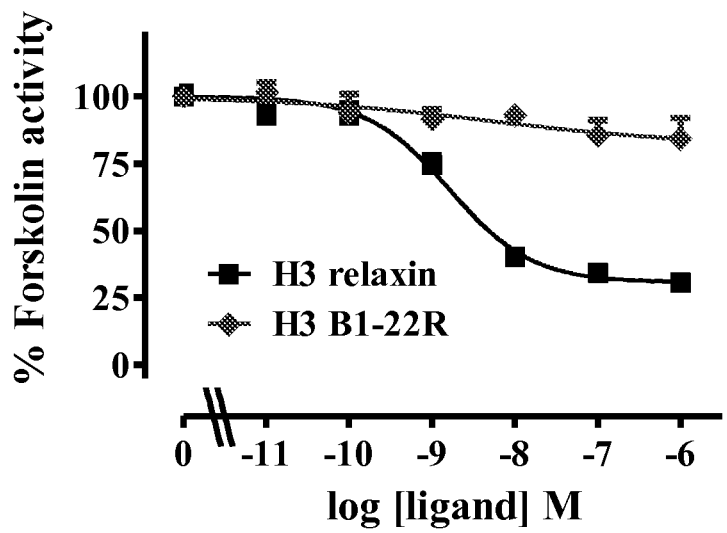
FIG. 3. cAMP activity in RXFP3 (GPCR135)-expressing cells in the presence of exemplary single chain polypeptide H3 B1-22R and/or native H3 (human) relaxin.
Figure 3:
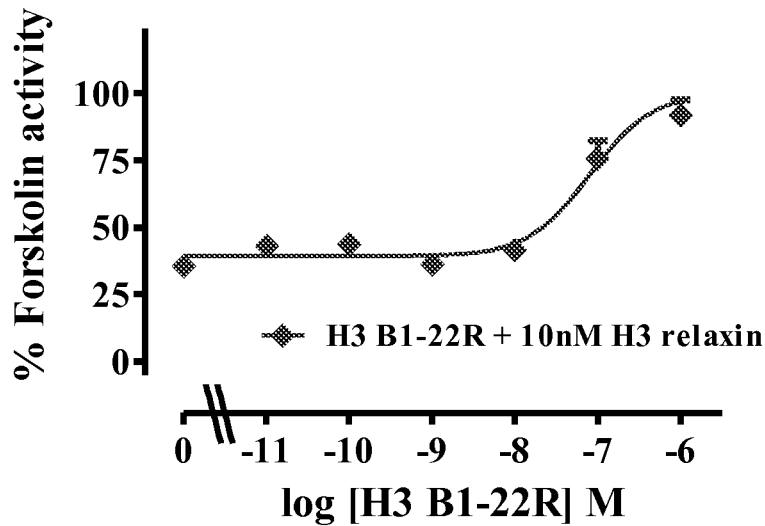

H3 relaxin inhibits cAMP activity in RXFP3-expressing cells (see FIG. 3A). However no such inhibition is observed with the B1-22R polypeptide (FIG. 3A). Rather, following a reduction in cAMP production to less than 50% in the presence of 10 nM H3 relaxin, the addition of increasing concentrations of B1-22R rescued cAMP levels towards 100% (FIG. 3B). Thus, the B1-22R single chain polypeptide is an antagonist of the RXFP3 receptor.

Figure 4:
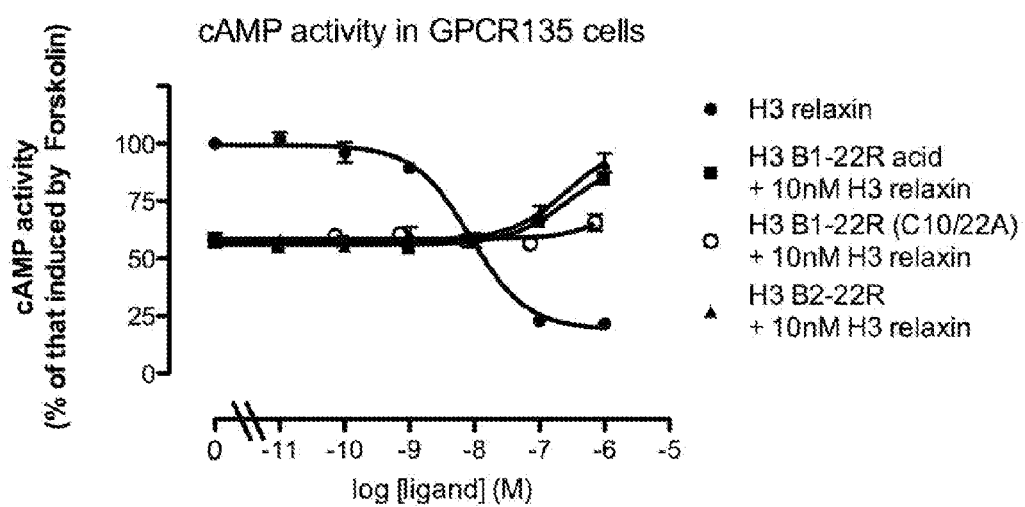
FIG. 4. cAMP activity in RXFP3 (GPCR135)-expressing cells in the presence of native H3 (human) relaxin alone, or native H3 relaxin and exemplary single chain polypeptide H3 B1-22R acid, H3 B1-22R(C10/22A) or H3 B2-22R.
Figure 5:
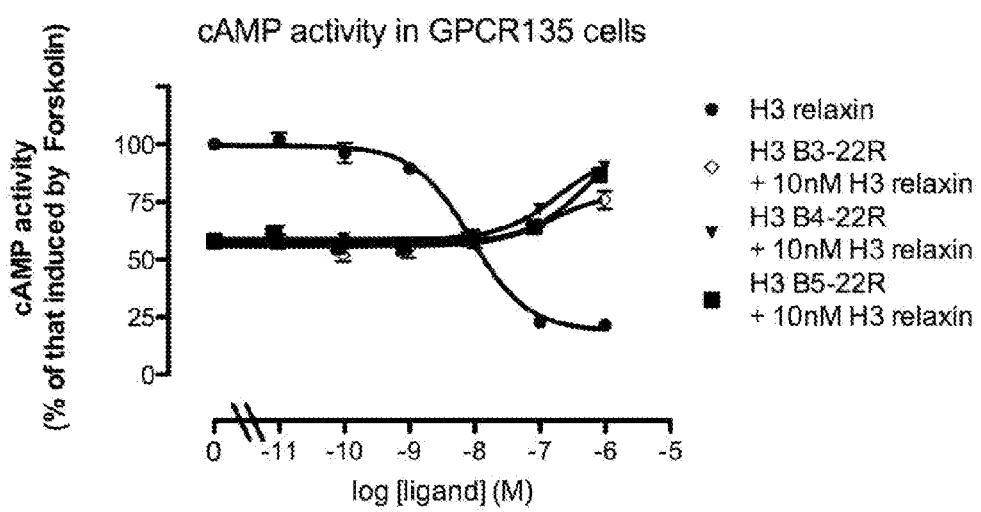
FIG. 5. cAMP activity in RXFP3 (GPCR135)-expressing cells in the presence of native H3 (human) relaxin alone, or native H3 relaxin and exemplary single chain polypeptide H3 B3-22R, H3 B4-22R, H3 B5-22R, H3 B6-22R or H3 B7-22R.
Figure 5:
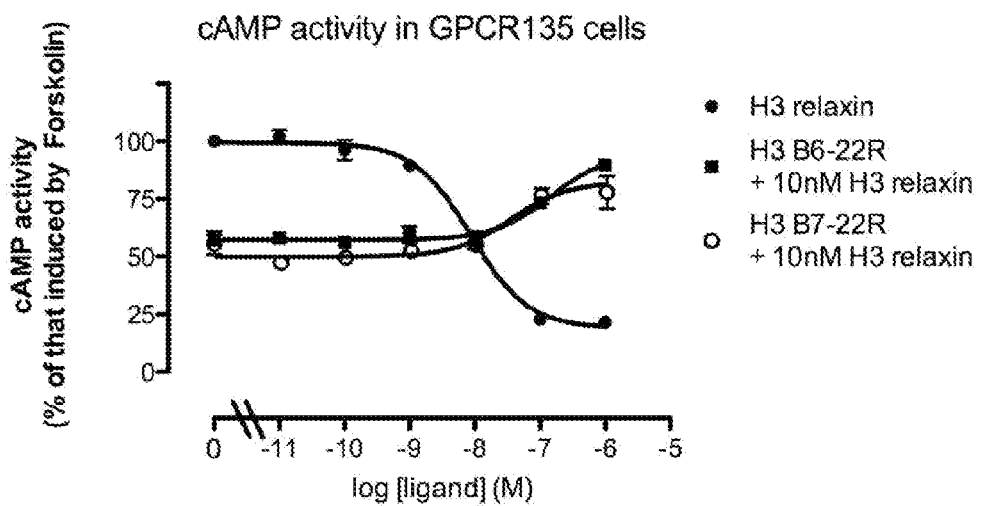

The abilities of the remaining single chain relaxin polypeptides to rescue cAMP levels in the presence of 10 nM H3 relaxin, and therefore antagonise RXFP3 were also tested. The results are shown in FIGS. 4 and 5. Whilst each of the single chain polypeptides was observed to have some degree of antagonising activity, H1-B22R appeared to have the greatest antagonist activity. Interestingly, the polypeptide B1-22R (C10/22A) displayed the lowest antagonist activity (FIG. 4).

Example 3

Binding Activities of Single Chain Relaxin Polypeptides Against RXFP4 and RXFP1

Figure 6:
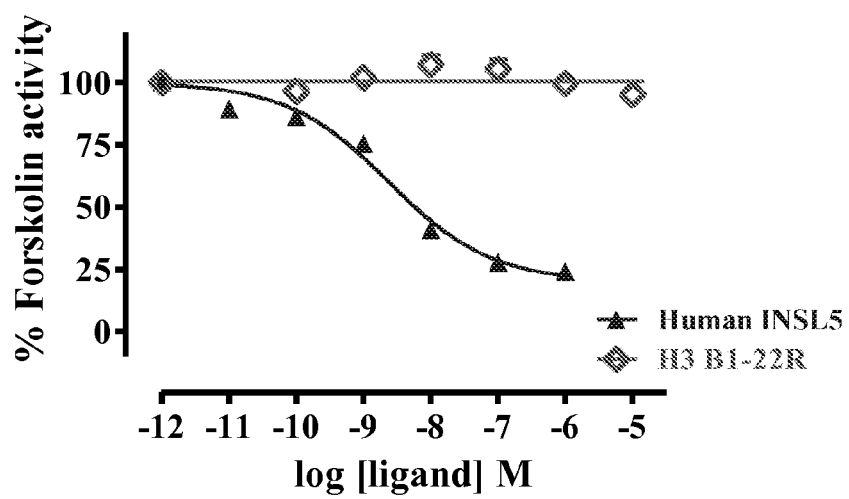
FIG. 6. cAMP activity in RXFP4-expressing cells in the presence of human INSL5 or exemplary single chain polypeptide H3 B1-22R (A), and in the presence of exemplary single chain polypeptide H3 B1-22R together with native H3 relaxin or human INSL5 (B).
Figure 6:
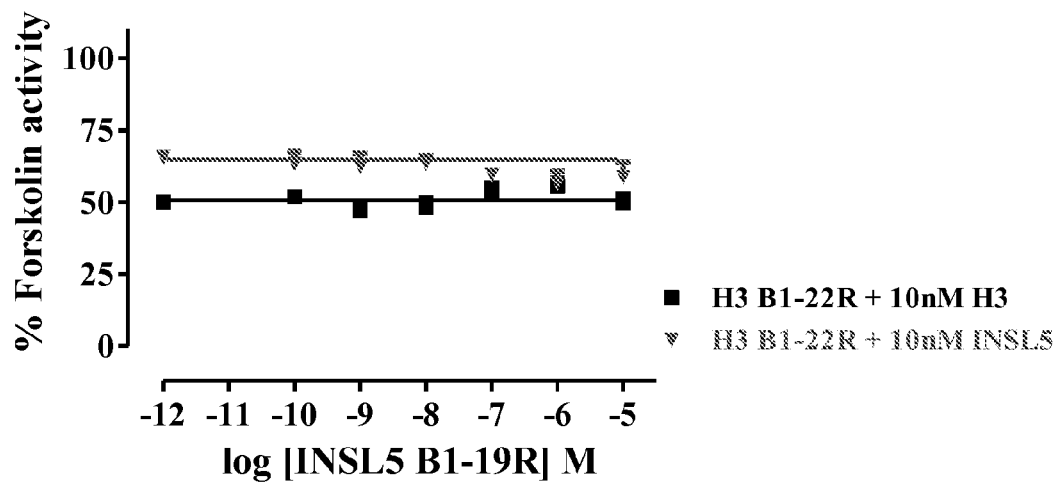

The B1-22R single chain polypeptide was tested for its ability to activate RXFP4 or antagonise the action of INSL5 or H3 relaxin at this receptor. INSL5 is the native ligand for RXFP4, however H3 relaxin is known to be able to bind and activate this receptor.

cAMP activity assays were carried out as described above in Example 2. As shown in FIG. 6A, B1-22R shows no agonist activity at RXFP4. Moreover, as shown in FIG. 6B, B1-22R also fails to show any observable antagonist activity at RXFP4 as determined by its inability to block either INSL5 or H3 relaxin stimulated RXFP4 activation.

Figure 7:
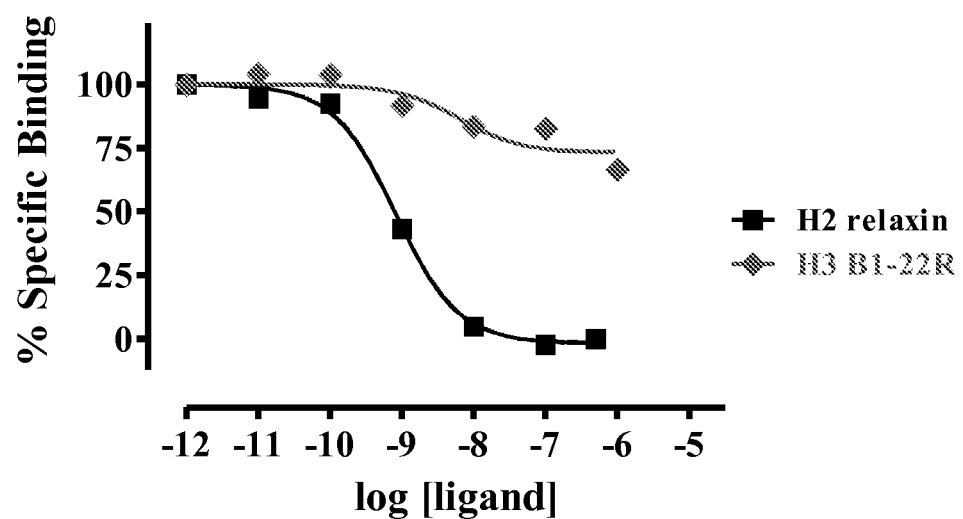
FIG. 7. Binding of H2 relaxin and exemplary single chain relaxin polypeptide H3 B1-22R to human RXFP1-expressing cells in the presence of europium (Eu)-labelled H2 relaxin.

Similarly, the B1-22R single chain polypeptide was tested for its ability to activate RXFP1 or antagonise the action of H2 relaxin at this receptor. To do so, binding assays were carried out essentially as described above in Example 2 except using HEK-293T cells transfected with RXFP1 and 300 μM of Eu-DTPA-H2 relaxin. As shown in FIG. 7, the B1-22R single chain polypeptide has a very poor affinity for the RXFP1 receptor, and thus does not act as an antagonist at this receptor.

The results of Examples 2 and 3 together demonstrate that B1-22R is a specific antagonist of RXFP3.

Example 4

Structural Analysis of Single Chain Relaxin Polypeptides

Figure 8:
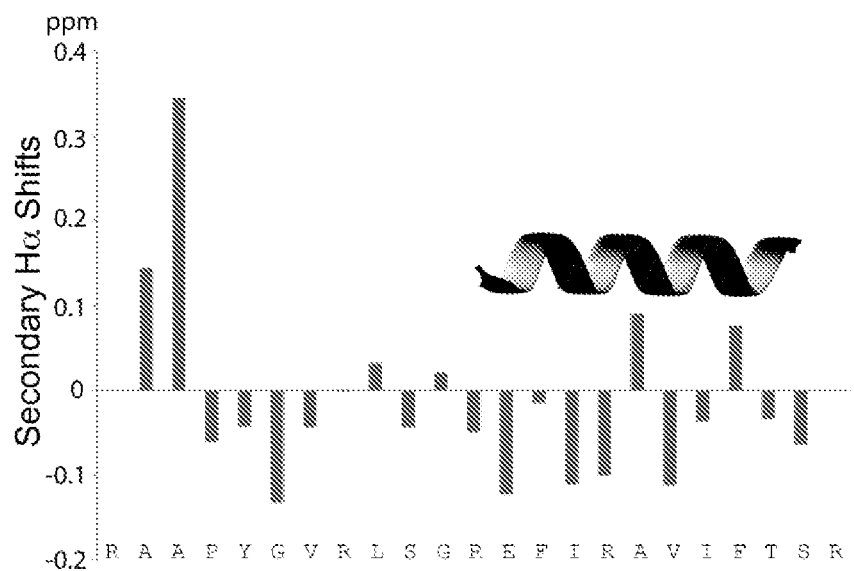
FIG. 8. Secondary Hα-shift analysis for R3 B1-22R. Stretches of negative values indicate a helical region and positive values indicate β-sheet. R3 B1-22R displays only small secondary shifts, suggesting a mainly random coil structure. The position of the B-chain helix in native relaxin-3 is indicated by a helix.

To investigate whether the single-chain analogues disclosed herein were able to adopt a native-like conformation in solution without structural support from the A-chain, the inventors examined the structural features of the analogue R3 B1-22R using two-dimensional NMR spectroscopy. R3 B1-22R (0.5 mg) was dissolved in 90% $H_2O$/10% $D_2O$ and subjected to solution NMR. 2D $^1H$ homonuclear TOCSY and NOESY were recorded with a mixing time of 200 ms at 298K and at 283K on a 600 MHz spectrometer. Spectrum was processed using Topspin 2.1 (Bruker) and analysed using CARA. Secondary shifts were calculated using the random coil chemical shifts described by Wishart et al (1995). NOESY and TOCSY spectra were recorded at 600 MHz and the spectra were of good quality in terms of line width and signal-to-noise, but had poor signal dispersion, as expected for an unstructured or helical peptide lacking a well-defined structural core. Resonance assignments were achieved by well-established sequential assignment strategies and an almost complete set of assignment was possible, with the exception of Arg1 and Arg23. Secondary Hα chemical shifts, i.e. differences between observed Hα chemical shifts and shifts seen in random coil peptides, are good indicators of the presence of secondary structure. As shown in FIG. 8, although there is a tendency towards negative shifts consistent with helical structure in the region Arg12-Ile19, which adopts a key helical structure in native relaxin-3, R3 B1-22R generally has secondary shifts close to zero, suggesting that it predominantly adopts a random coil like conformation in solution. This was confirmed by analysis of NOE data, which revealed the presence of very few medium range NOEs that are typically observed in helical peptides, and also by CD spectroscopy analysis. Thus, it appears that R3 B1-22R is flexible in solution, and probably only adopts the correct conformation for binding upon interaction with the RXFP3 receptor.

Example 5

Regulation of Alcohol Self-Administration Following Treatment with Single Chain Relaxin Polypeptides The inventors then tested the ability of the selective RXFP3 receptor antagonist B1-22R for effects on self-administration of alcohol in alcohol-preferring (iP) rats.

Rats were trained to stably administer 10% ethanol during daily operant session (n=18 rats) and then implanted with guide cannulae aimed at the lateral cerebral ventricle. Following a 7 day recovery period, the rats were re-stabilised on alcohol self-administration under fixed-ratio 3 (FR3) conditions and the effect of B1-22R was examined.

Figure 9:
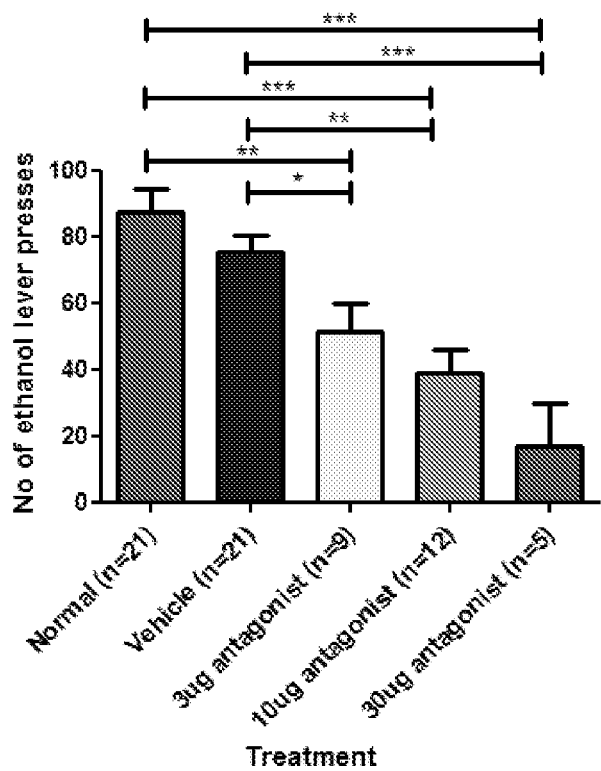
FIG. 9. Operant responding (total ethanol lever presses) for alcohol in alcohol-preferring (iP) rats and attenuation by the single chain, selective RXFP3 antagonist B1-22R. All data are expressed as (±SEM). *p<0.05, p<0.01, *p<0.001.

Rats were administered 3 μg, 10 μg or 30 μg of the B1-22R antagonist. As shown in FIG. 9, a significant decrease in ethanol lever presses was observed in rats injected with the B1-22R antagonist compared to normal and vehicle responding. The effect observed was dose-dependent.

The inventors also carried out experiments to determine if the effects may be due to disruption in locomotor skills. No significant difference was observed between the locomotor skills of rats administered B1-22R (10 μg) compared to those administered vehicle, in terms of floor plane moves or floor plane distance over time periods between 0 and 45 minutes post administration (data not shown) indicating that, like R3(Δ23-27)/15, B1-22R does not effect locomotor activity.

REFERENCES

Bathgate et al., 2006, *Pharmacol Rev* 58:7-31
Shaham et al., 2003, *Psychopharmacology* 168: 3-20
Wishart et al., 1995, *J Biomol NMR* 5:67

The invention claimed is:

1. A single chain relaxin polypeptide comprising a relaxin B chain, the polypeptide being truncated by up to five amino acids at the C-terminus of the relaxin-3 B chain; wherein the truncated C-terminal amino acid(s) are replaced with a basic amino acid, wherein one or more cysteine residues in the relaxin-3 B chain sequence are replaced by neutral amino acids, and wherein the polypeptide is selective or specific for the RXFP3 receptor.

2. The polypeptide of claim 1 wherein the basic amino acid residue is arginine.

3. The polypeptide of claim 1 wherein the B chain sequence is from human relaxin-3 and the C-terminal sequence GGSRW (residues 23-27 of SEQ ID NO: 2) is replaced by R.

4. The polypeptide of claim 1 wherein the neutral amino acids are serine or alanine residues.

5. The polypeptide of claim 1 wherein the B chain sequence is from human relaxin-3 and the cysteine residues at positions 10 and 22 of the native human relaxin-3 sequence are replaced by serine residues.

6. The polypeptide of claim 1 comprising a C-terminal amide group.

7. The polypeptide of claim 1 further comprising a truncation of up to five amino acids from the N-terminus of the relaxin-3 B chain when compared to the native relaxin-3 sequence.

8. The polypeptide of claim 7 wherein the truncation is of up to about 4 amino acids from the N-terminus.

9. The polypeptide of claim 1 wherein the polypeptide comprises or consists of the amino acid sequence set forth in one of SEQ ID NOs:4 to 13.

10. The polypeptide of claim 1 wherein the polypeptide is an antagonist of the RXFP3 receptor.

11. The polypeptide claim 1 wherein the polypeptide is a selective or specific antagonist of the RXFP3 receptor.

12. A polynucleotide encoding a single chain relaxin polypeptide comprising a relaxin B chain, the polypeptide being truncated by up to five amino adds at the C-terminus of the relaxin-3 B chain; wherein the truncated C-terminal amino acid(s) are replaced with a basic amino acid, wherein one or more cysteine residues in the relaxin-3 B chain sequence are replaced by neutral amino adds, and wherein the polypeptide is selective or specific for the RXFP3 receptor.

13. A pharmaceutical composition comprising a polypeptide according to claim 1, optionally together with one or more pharmaceutically acceptable carriers, excipients or diluents.

14. A method for the inhibition of alcohol use, abuse and/or addiction, or alcohol seeking behaviour associated with alcohol abuse and/or addiction, the method comprising administering to a subject in need thereof an effective amount of a polypeptide according to claim 1.

15. A method of antagonizing the binding relaxin-3 to the RXFP3 receptor comprising administering an effective amount of the polypeptide according to claim 1.

* * * * *

SEQUENCE LISTING

<160> NUMBER OF SEQ ID NOS: 13

<210> SEQ ID NO 1
<211> LENGTH: 24
<212> TYPE: PRT
<213> ORGANISM: Homo sapiens

<400> SEQUENCE: 1

Asp Val Leu Ala Gly Leu Ser Ser Cys Cys Lys Trp Gly Cys Ser
1               5                   10                  15

Lys Ser Glu Ile Ser Ser Leu Cys
            20

<210> SEQ ID NO 2
<211> LENGTH: 27
<212> TYPE: PRT
<213> ORGANISM: Homo sapiens

<400> SEQUENCE: 2

Arg Ala Ala Pro Tyr Gly Val Arg Leu Cys Gly Arg Glu Phe Ile Arg
1               5                   10                  15

Ala Val Ile Phe Thr Cys Gly Gly Ser Arg Trp
            20                  25

<210> SEQ ID NO 3
<211> LENGTH: 27
<212> TYPE: PRT
<213> ORGANISM: Artificial Sequence
<220> FEATURE:
<223> OTHER INFORMATION: Synthetic (modified) sequence

<400> SEQUENCE: 3

Arg Ala Ala Pro Tyr Gly Val Arg Leu Ser Gly Arg Glu Phe Ile Arg
1               5                   10                  15

Ala Val Ile Phe Thr Ser Gly Gly Ser Arg Trp
            20                  25

<210> SEQ ID NO 4
<211> LENGTH: 23
<212> TYPE: PRT
<213> ORGANISM: Artificial Sequence
<220> FEATURE:
<223> OTHER INFORMATION: Synthetic (modified) sequence
<220> FEATURE:
<221> NAME/KEY: MISC_FEATURE
<222> LOCATION: (23)..(23)
<223> OTHER INFORMATION: C-terminal -NH2 group

<400> SEQUENCE: 4

Arg Ala Ala Pro Tyr Gly Val Arg Leu Ser Gly Arg Glu Phe Ile Arg
1               5                   10                  15

Ala Val Ile Phe Thr Ser Arg
            20

<210> SEQ ID NO 5
<211> LENGTH: 23
<212> TYPE: PRT
<213> ORGANISM: Artificial Sequence
<220> FEATURE:
<223> OTHER INFORMATION: Synthetic (modified) sequence

```
<400> SEQUENCE: 5

Arg Ala Ala Pro Tyr Gly Val Arg Leu Ala Gly Arg Glu Phe Ile Arg
1               5                   10                  15

Ala Val Ile Phe Thr Ala Arg
            20

<210> SEQ ID NO 6
<211> LENGTH: 23
<212> TYPE: PRT
<213> ORGANISM: Artificial Sequence
<220> FEATURE:
<223> OTHER INFORMATION: Synthetic (modified) sequence
<220> FEATURE:
<221> NAME/KEY: MISC_FEATURE
<222> LOCATION: (23)..(23)
<223> OTHER INFORMATION: C-terminal -OH group

<400> SEQUENCE: 6

Arg Ala Ala Pro Tyr Gly Val Arg Leu Ser Gly Arg Glu Phe Ile Arg
1               5                   10                  15

Ala Val Ile Phe Thr Ser Arg
            20

<210> SEQ ID NO 7
<211> LENGTH: 22
<212> TYPE: PRT
<213> ORGANISM: Artificial Sequence
<220> FEATURE:
<223> OTHER INFORMATION: Synthetic (modified) sequence

<400> SEQUENCE: 7

Arg Ala Ala Pro Tyr Gly Val Arg Leu Ser Gly Arg Glu Phe Ile Arg
1               5                   10                  15

Ala Val Ile Phe Thr Ser
            20

<210> SEQ ID NO 8
<211> LENGTH: 22
<212> TYPE: PRT
<213> ORGANISM: Artificial Sequence
<220> FEATURE:
<223> OTHER INFORMATION: Synthetic (modified) sequence

<400> SEQUENCE: 8

Ala Ala Pro Tyr Gly Val Arg Leu Ser Gly Arg Glu Phe Ile Arg Ala
1               5                   10                  15

Val Ile Phe Thr Ser Arg
            20

<210> SEQ ID NO 9
<211> LENGTH: 21
<212> TYPE: PRT
<213> ORGANISM: Artificial Sequence
<220> FEATURE:
<223> OTHER INFORMATION: Synthetic (modified) sequence

<400> SEQUENCE: 9

Ala Pro Tyr Gly Val Arg Leu Ser Gly Arg Glu Phe Ile Arg Ala Val
1               5                   10                  15

Ile Phe Thr Ser Arg
            20
```

```
<210> SEQ ID NO 10
<211> LENGTH: 20
<212> TYPE: PRT
<213> ORGANISM: Artificial Sequence
<220> FEATURE:
<223> OTHER INFORMATION: Synthetic (modified) sequence

<400> SEQUENCE: 10

Pro Tyr Gly Val Arg Leu Ser Gly Arg Glu Phe Ile Arg Ala Val Ile
1               5                   10                  15

Phe Thr Ser Arg
            20

<210> SEQ ID NO 11
<211> LENGTH: 19
<212> TYPE: PRT
<213> ORGANISM: Artificial Sequence
<220> FEATURE:
<223> OTHER INFORMATION: Synthetic (modified) sequence

<400> SEQUENCE: 11

Tyr Gly Val Arg Leu Ser Gly Arg Glu Phe Ile Arg Ala Val Ile Phe
1               5                   10                  15

Thr Ser Arg

<210> SEQ ID NO 12
<211> LENGTH: 18
<212> TYPE: PRT
<213> ORGANISM: Artificial Sequence
<220> FEATURE:
<223> OTHER INFORMATION: Synthetic (modified) sequence

<400> SEQUENCE: 12

Gly Val Arg Leu Ser Gly Arg Glu Phe Ile Arg Ala Val Ile Phe Thr
1               5                   10                  15

Ser Arg

<210> SEQ ID NO 13
<211> LENGTH: 17
<212> TYPE: PRT
<213> ORGANISM: Artificial Sequence
<220> FEATURE:
<223> OTHER INFORMATION: Synthetic (modified) sequence

<400> SEQUENCE: 13

Val Arg Leu Ser Gly Arg Glu Phe Ile Arg Ala Val Ile Phe Thr Ser
1               5                   10                  15

Arg
```